US006326402B1

(12) United States Patent
Kun et al.

(10) Patent No.: US 6,326,402 B1
(45) Date of Patent: Dec. 4, 2001

(54) METHODS FOR TREATING VIRAL INFECTIONS USING A COMPOUND CAPABLE OF INHIBITING MICROTUBULES

(75) Inventors: Ernest Kun, Mill Valley; Jerome Mendeleyev, Tiburon, both of CA (US)

(73) Assignee: Octamer, Inc., Berkeley, CA (US)

( * ) Notice: Subject to any disclaimer, the term of this patent is extended or adjusted under 35 U.S.C. 154(b) by 0 days.

(21) Appl. No.: 09/133,071

(22) Filed: Aug. 12, 1998

(51) Int. Cl.[7] .................. A61K 31/19; A61K 31/215; A61K 31/195; A61K 31/135; A61K 31/12

(52) U.S. Cl. .................. 514/557; 514/529; 514/561; 514/568; 514/646; 514/647; 514/679

(58) Field of Search .................. 514/557, 529, 514/561, 568, 646, 647, 679

(56) References Cited

U.S. PATENT DOCUMENTS

| 3,097,137 | 7/1963 | Beer et al. ............... 167/65 |
| 3,205,220 | 9/1965 | Svoboda et al. .......... 260/236 |
| 3,352,868 | 11/1967 | Neuss et al. ............. 260/287 |
| 3,370,057 | 2/1968 | Svoboda et al. .......... 260/236 |
| 3,387,001 | 6/1968 | Hargrove ............... 260/287 |
| 3,392,173 | 7/1968 | Hargrove ............... 260/286 |
| 3,887,565 | 6/1975 | Jones et al. ............ 260/287 R |
| 3,890,325 | 6/1975 | Smith et al. ............ 260/287 R |
| 3,944,554 | 3/1976 | Tafur ................... 260/287 |
| 3,954,773 | 5/1976 | Neuss et al. ............ 260/286 R |
| 4,160,767 | 7/1979 | Miller et al. ............ 260/244.4 |
| 4,522,750 | 6/1985 | Ades et al. ............. 260/112 R |
| 4,667,030 | 5/1987 | Cullinan ............... 540/478 |

FOREIGN PATENT DOCUMENTS

| 811110 | 5/1974 | (BE) . |
| 813168 | 10/1974 | (BE) . |
| WO98/42328 | 10/1998 | (WO) . |
| WO99/20263 | 4/1999 | (WO) . |

OTHER PUBLICATIONS

Li, C.H. edit. "Hormonal Proteins and Peptides" vol. VI pp 107–204 Academic Press, N.Y.(1978).
Li, C.H. edit. "Hormonal Proteins and Peptides" vol. VI: 57–105 Academic Press, N.Y. (1978).
Li, C.H. edit. Hormonal Proteins and Peptides vol. VI p 150 Academic Press (1978).
Meltzer, et al., "Thyroxine Analogs", *J. Org. Chem.*—22:1577–1581 (1957).
Mendeleyev, et al., "Structural Specificity and Tumoricidal Action of Methyl–3,5–Diiodo–4–(4'–Methoxyphenoxy) Benzoate (DIME)", *Int. J. Oncology*—10:689–695 (1997).
Money, et al. "The Effect of Various Thyroxine Analogues on Suppression of $I^{131}$ Uptake by the Rat Thyroid[1]", Endocrinology—64:123–125 (1959).
Money, et al., "The Effect of Change in Chemical Structure of Some Thyroxine Analogues on the Metamorphosis of *Rana pipiens* Tadpoles[1]", Endocrinology—63:20–28 (1958).

Osborne, et al., "Effects of Estrogens and Antiestrogens on Growth of Human Breast Cancer Cells in Athymic Nude Mice[1]", *Cancer Res.*—45:584–590 (1985).

Ozzello, et al., "Behavior of Tumors Produced by Transplantation of Human Mammary Cell Lines in Athymic Nude Mice*", *Eur. J. Cancer*—16:553–559 (1980).

Rygaard, et al., "Heterotransplantation of a Human Malignant Tumour to Nude Mice", *Acta Pathol. Microbiol. Scand.* 77:758–760 (1969).

Siebert, et al., "Clonal Variation of MCF–7 Breast Cancer Cells in Vitro and in Athymic Nude Mice", *Cancer Research*—43:2223–2239 (1983).

Spudich, "How molecular motors work", *Nature*—372: 515–518 (1994).

Stasilli, et al., "Antigoitrogenic and Calorigenic Activities of Thyroxine Analogues in Rats[1]", *Endocrinology*—64:62–82 (1959).

Wang, et al., "Microtubule–Interfering Agents Activate c–Jun N–Terminal Kinase/Stress–Activated Protein Kinase Through Both Ras and Apoptosis Signal–Regulating Kinase Pathways*", *J. Biol. Chem.*—273(9):4828–4936 (1998).

Warri, et al., "Estrogen Suppression of erbB2 Expression is Associated with Increased Growth Rate of ZR–75–1 Human Breast Cancer Cells In Vitro and in Nude Mice", *Int' J. Cancer* 49:616–623 (1991).

Zhen, et al., "Cellular Analysis of the Mode of Action of Methyl–3, 5–Diiodo–4–(4'–Methoxypheoxy) Benzoate (DIME) on Tumor Cells" *Int. J. of Oncology*—10:905–910 (1997).

Borrows, et al., "The Sythesis of Thyroxine and Related Substances. Part I. The Preparation of Tyrosine and Some of its Derivatives, and a New Route to Thyroxine", *J. Chem. Soc.*—S185–S190 (1949).

(List continued on next page.)

*Primary Examiner*—Russell Travers
(74) *Attorney, Agent, or Firm*—Albert P. Halluin; J. David Smith; Howrey Simon Arnold & White, LLP

(57) ABSTRACT

The present invention is directed to a method for inhibiting viral replication and treating viral infections by administering a pharmaceutically effective amount of a compound capable of binding a microtubule such as a diiodo thyronine analogue having no significant hormonal activity. The present invention also features novel pharmaceutical compositions comprising the same.

12 Claims, 1 Drawing Sheet

OTHER PUBLICATIONS

Buki, et al., "Inhibition of Migration of MDA–MB–231 Cells by Methyl–3,5–Diiodo–4–(4'–Methoxyphenoxy) Benzoate (DIME)", *Int. J. of Oncology*—11:1247–1250 (1997).

Buki, et al., "Inhibition of the GTP–Dependent Polymerization of Tubulin by Methyl–3,5–Diiodo–4–(4'–Methoxyphenoxy) Benzoate (DIME)", *Int. J. of Oncology*—10: 911–913 (1997).

Case, et al., "The Directional Preference of Kinesin Motors is Specified by an Element Outside of the Motor Catalytic Domain", *Cell*—90:959–966 (1997).

Clayton, et al., "The Synthesis of Thyroxine and Related Substances. Part VIII * The Preparation of Some Halogeno—and Nitro–Diphenyl Ethers", *J. Chem Soc.* Part VIII:—2467–2473 (1951).

Crowder, et al., "Bisbenzylisoquinolines. Part II.[1] The Synthesis of 5–(2–Aminoethyl)–4'–carboxy–2:3–Dimethoxydiphenyl Ether", *J. Chem Soc.*—438:2142–2149 (1958).

DiCicco, "Seventy–Ninth Annual Meeting of the American Association for Cancer Research" et al., Proc. Amer. Assoc. for Cancer Res. 177 Abstract No. 1213 (1988).

Gemmil, et al., "3–Iodo–, 3,3'–Diiodo–and 3,3'–Diiodo–5–Bromothyronine[1]", *J. Am. Chem. Soc.*—78:2434–2436 (1956).

Gewert, et al., "Inhibition of Cell Division by Interferons", *Eur. J. Biochem.*—116:487–494 (1981).

Grinberg, et al., "Studies with Mouse Pituitary Thyrotropic Tumors V. Effect of Various Thyroxine Analogs on Growth and Secretion*", *Cancer Research*—22:835–841 (1962).

Henningsen, et al., "Reversal in the Direction of Movement of a Molecular Motor", *Nature*—389:93–95 (1997).

Howard, "The Movement of Kinesin Along Microtubules", *Ann. Rev. Physiology*—58:703–729 (1996).

Kirsten, et al., "Unusual Potentiation by Vinca Alkaloids of the Cytostatic and Cytocidal Action of Methyl–3,5 – Diiodo–4(4'–Methoxyphenoxy) Benzoate (DIME) and its Nonhydrolyzable Ethanone Analog (DIPE) on MDA–MB–231 Human Mammary Cancer Cells", *Int. J. of Oncology*—13:49–55 (1998).

Kumaoka, et al., "The Effect of Thyroxine Analogues on a Transplantable Mouse Pituitary Tumor[1]", *Endocrinology*—66:32–38 (1960).

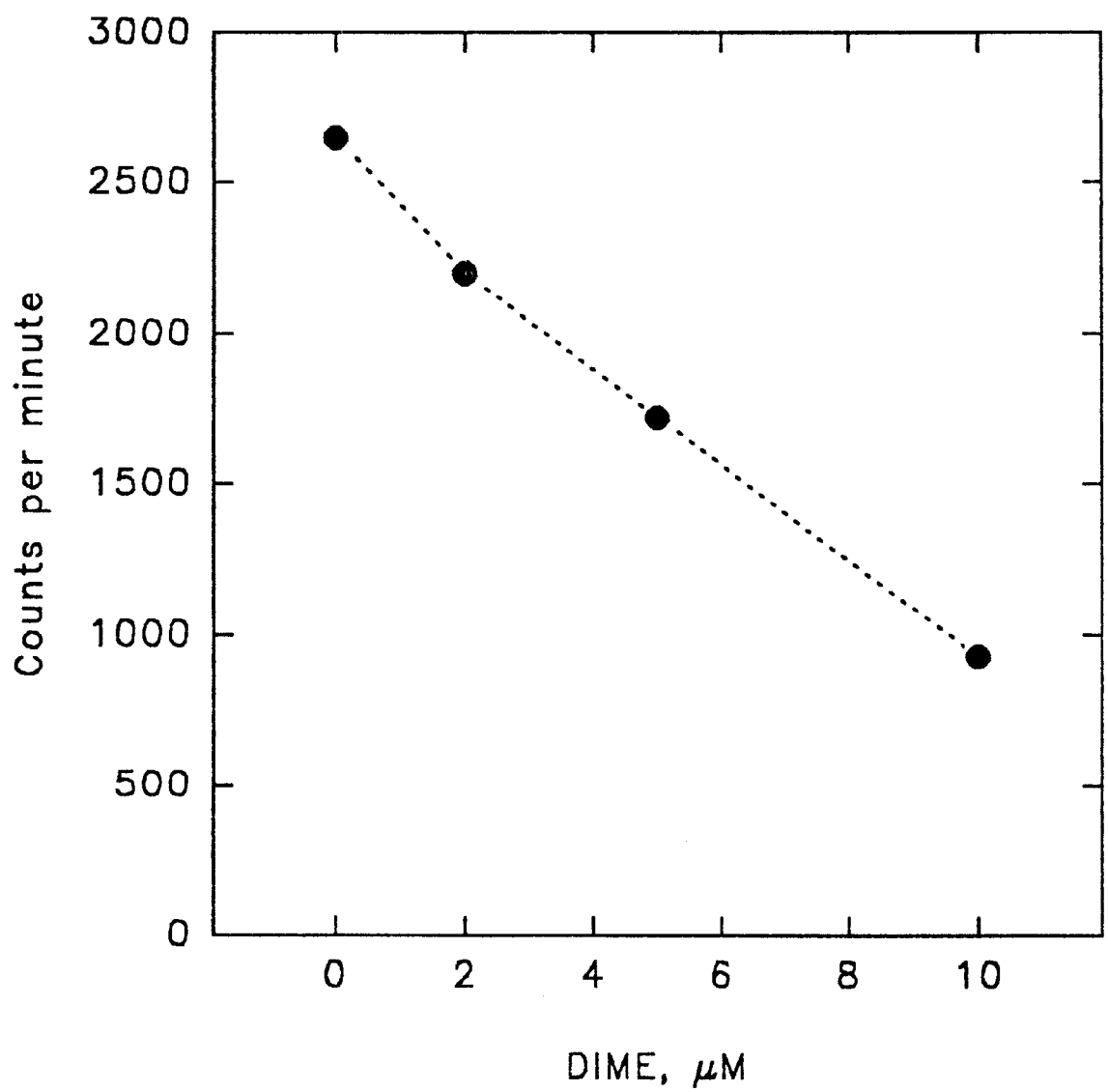

METHODS FOR TREATING VIRAL INFECTIONS USING A COMPOUND CAPABLE OF INHIBITING MICROTUBULES

The present invention is in the field of biochemistry and pharmacology. Specifically, the present invention relates to methods for inhibiting viral replication and treating viral infections by administering a pharmaceutically effective amount of a compound capable of binding microtubules or inhibiting microtubule formation or tubulin polymerization such as diiodo thyronine analogues. The invention also relates to pharmaceutical compositions comprising the same.

BACKGROUND OF THE INVENTION

The high degree of infectiousness and fast reproduction cycle of viruses within host organisms make viruses a nuisance and a health hazard. There is no simple treatment of viral diseases. Viruses are not susceptible to antibiotics. The only available treatment of viral diseases is chemotherapy utilizing viral replication inhibitors in host cells *The Merck Manual*, 170 (1982), 14th Ed.). Examples of these chemical agents are idoxuridine, acyclovir, ribavirin, vidarabine, gancyclovir, adenine arabinoside (ABA-A) and AZT. These, and other viral replication inhibitors, however, are cytotoxic, hepatotoxic, neurotoxic, nephrotoxic and teratogenic (*Virus Diseases*, 1–6 (1978), Crown Publishers, N.Y.).

Human immunodeficiency virus (HIV) infections known as acquired immunodeficiency syndrome (AIDS) presently constitute a worldwide health hazard. HIV infections are almost always fatal due to a weakened immunoresistance, leading to opportunistic infections, malignancies and neurologic lesions. There are few effective treatments for AIDS other than the treatment of the opportunistic infections, neoplasms and other complications. Available cytostatic (AZT) and antiviral (acyclovir) drugs are extremely toxic and cause severe adverse reactions. Novel classes of protease inhibitors have not been satisfactorily studied over the long term to assure continued efficacy and to assess long term side effects. Thus it would be highly desirable to have available an effective and yet nontoxic treatment of viral diseases, in particular, AIDS.

Herpes simplex virus type-1 and 2 are also widespread infections. They may occur in AIDS patients as one of the opportunistic infections. Type-1 HSVstrain (HSV-1) commonly causes herpes labialism located on a lip, and keratitis, an inflammation of the cornea. Type-2 HSV is usually located on or around the genital area and is generally transmitted primarily by direct contact with herpetic sores or lesions. HSV-2 has been related to the development of uterine cancer. Herpes simplex virus is very infectious and is rapidly and easily transferable by contact. There is no specific therapy for this extremely painful viral infection. Current treatment of HSV infections is limited primarily to systemic administration of the above-mentioned antiviral drugs with corresponding adverse side affects. The antiviral agents used for treatment are non-selective inhibitors of HSV replication affecting the replication of normal cells as well. Therefore, when used in doses large enough to inactivate all of the active herpes viruses dormant in the sensory ganglia, these compounds may also be highly disruptive to host cell DNA replication. Thus, it would be advantageous to have available non-toxic treatment of HSV infections.

Cytomegalovirus (CMV), a dangerous co-infection of HIV, is a subgroup of highly infectious viruses having the propensity for remaining latent in man. CMVs are very common among the adult population and as many as 90% of adults have been exposed to and experienced CMV infections. CMVs are normally present in body liquids such as blood, lymph, saliva, urine, feces, milk, etc. CMV infections may cause abortion, stillbirth, postnatal death from hemorrhage, anemia, and severe hepatic or CNS damage. Particularly dangerous are CMV infections afflicting AIDS patients, where CMV may cause pulmonary, gastrointestinal or renal complications. There is no specific therapy for CMV infection. Unlike many other viruses, CMV is resistant to acyclovir, and to other known antiviral drugs. There is a great need to provide effective treatments for CMV infections.

Recently, it was discovered that agents that bind and/or inhibit the assembly or formation of microtubules are effective in inhibiting or preventing certain cancers. This is the subject of U.S. Ser. Nos. 08/655,267 and 08/833,272 filed on Jun. 4, 1996 and Apr. 3, 1997 respectively. The disclosures of both applications are herein expressly incorporated by reference in their entirety. Ketone diiodo thyronine analogues useful for treating cancer are the subject of U.S. Ser. No. 08/956,711 filed Oct. 23, 1997. The disclosure of this application is also herein expressly incorporated by reference in its entirety.

New classes of therapeutic agents providing new points of intervention for inhibiting or preventing viral infection and replication would be highly useful. It has been discovered that agents that bind and/or inhibit the assembly or formation of microtubules are effective in inhibiting or preventing viral infection and/or replication.

SUMMARY OF THE INVENTION

One aspect of the invention is a method for treating viral infections by administering a pharmaceutically effective amount of a compound capable of binding to microtubules or inhibiting microtubule formation. Preferably, the compound is substantially toxic only to cells that are infected with the target virus. Also, preferably, the compound is selectively permeable to cells infected with the target virus.

Exemplary compounds within the scope of the invention include diiodo thyronine analogues having no significant hormonal activity, particularly methyl 3,5-diiodo-4-(4'-methoxy phenoxy) benzoate ("DIME"), 1-[3,5-diiodo-4-(4'-methoxyphenoxy)-phenyl]-ethanone ("DIPE") and 1-[3,5-diiodo-4-(4'-methoxyphenoxy)-phenyl]-propanone ("DIPP").

The method for treating viral infections generally involves administering to a mammal an amount of a compound that binds to and inhibits microtubule formation that is effective to inhibit or prevent viral replication or to treat viral infection.

Yet another aspect of the invention is novel pharmaceutical compositions comprising a pharmaceutically effective amount of a compound capable of binding to microtubules or inhibiting microtubule formation. One such class of compounds are diiodo thyronine analogues having no significant hormonal activity, particularly methyl 3,5-diiodo-4-(4'-methoxy phenoxy) benzoate ("DIME"), 1-[3,5-diiodo-4-(4'-methoxyphenoxy)-phenyl]-ethanone ("DIPE") and 1-[3,5-diiodo-4-(4'-methoxyphenoxy)-phenyl]-propanone ("DIPP").

In one embodiment, diiodo thyronine analogues useful in the methods of the present invention are compounds having the structural formula:

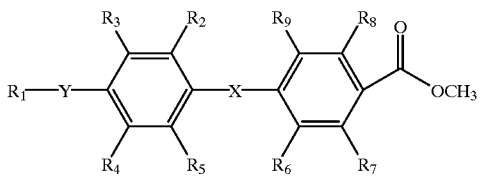

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: H, ($C_1$–$C_4$) alky, ($C_1$–$C_4$) alkenyl, ($C_1$–$C_4$) alkynyl, hydroxy, ($C_1$–$C_4$) alkoxy and halogen; and $R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy, halogen, $NO_2$ and $NH_2$.

In another illustrative embodiment, diiodo thyronine analogues useful in the methods of the present invention are compounds having the structural formula:

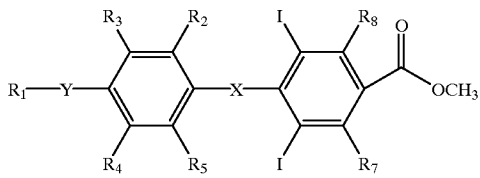

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy and halogen; and $R_7$ and $R_8$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy, halogen, $NO_2$ and $NH_2$.

In a preferred embodiment of the invention the diiodo thyronine analogue is methyl 3,5-diiodo-4-(4'-methoxyphenoxy) benzoate ("DIME").

Ketone diiodo thyronine analogues useful in the methods of the present invention are generally compounds having the structural formula:

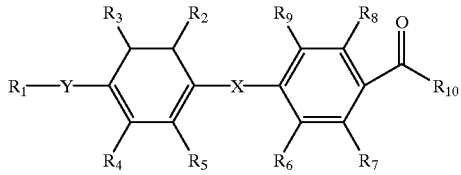

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkyl, hydroxyl, (($C_1$–$C_4$) alkoxy and halogen;

$R_6$, $R_7$, $R_8$, and $R_9$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$, and NH2; and $R_{10}$ is selected from the group consisting of ($C_1$–$C_4$) alkyl, ($C_1$–$C_4$) alkenyl, and ($C_1$–$C_4$) alkynyl.

In a preferred embodiment, compounds useful in the methods of the present invention are compounds having the structural formula:

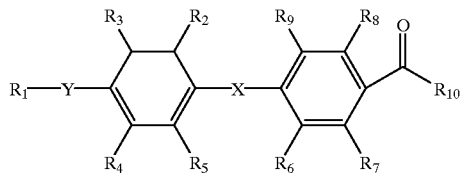

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: $H_1$, ($C_1$–$C_4$) alkyl, ($C_1$–$C_4$) alkenyl, ($C_1$–$C_4$) alkynyl, hydroxyl, ($C_1$–$C_4$) alkoxy and halogen; $R_7$ and $R_8$ are each independently selected from the group consisting of: $H_1$ ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$; and $R_{10}$ is selected from the group consisting of ($C_1$ to $C_4$) alkyl, ($C_1$–$C_4$) alkenyl and ($C_1$ to $C_4$) alkynyl.

In a particularly preferred embodiment, the compound is selected from the group consisting of 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP).

Other exemplary compounds capable of binding microtubules and thereby inhibiting formation or polymerization of the same include the vinca alkaloids and analogues thereof and taxol. Preferred compounds are substantially toxic only to cells that are infected with the target virus. Especially preferred compounds are selectively permeable to virally infected cells.

BRIEF DESCRIPTION OF THE DRAWING

FIG. 1 demonstrates the reverse transcriptase concentration in cell supernatant in correlation with "DIME" concentration. These data demonstrate that reverse transcriptase activity (an indication of viral replication) decreases with increased "DIME" concentration.

DETAILED DESCRIPTION OF THE INVENTION

The present invention relates to methods of inhibiting viral replication and treating viral infections in mammals with compounds capable of binding or inhibiting the formation or polymerization of microtubules. Preferred compounds useful in the present invention are analogues of diiodo thyronine that are characterized as having no significant hormonal activity. The present invention is based, in part, on the surprising discovery that certain analogues of thyroxine that do not exhibit hormonal activity are potent inhibitors of viral replication. The preferred diiodo thyronine analogue is referred to herein as DIME.

Thyroxine, an amino acid of the thyroid gland (*Merck Index,* 1989, 9348:1483) and analogues thereof are well-known in the art. It is well established in the literature that thyroid hormones, specifically thyroxine T3 and T4, have two distinct types of biological actions: one on cell metabolism, the second on cell differentiation and development (Jorgensen, 1978, "Thyroid Hormones and Analogues II. Structure-Activity Relationships," In: *Hormonal Proteins and Peptides,* Vol. VI, pp. 107–204, C. H. Li, ed., Academic Press, NY). For example, thyroxine suppresses uptake of iodine by the thyroid (Money et al., 1959, Endocrinology 64:123–125) and induces cell differentiation as studied by tadpole metamorphosis (Money et al., 1958, *Endocriniology* 63:20–28). Additionally, thyroxine and certain analogues thereof depress growth of non-malignant mouse pituitary thyrotropic tumors (Kumaoka et al., 1960, *Endocrinology* 66:32–38; Grinberg et al., 1962, *Cancer Research* 22:835–841).

The structural requirements of thyroxine and thyroxine analogues for metabolic sitimulation and induction of cell differentiation are not identical (Jorgensen, 1978, "Thyroid Hormones and Analogues II. Structure-Activity Relationships," In: Hormonal Proteins and Peptides, Vol. VI, p. 150, C. H. Li, ed., Academic Press, NY). For example, Money et al., found that there is no correlation between suppression of thyroid iodine uptake and induction of tadpole metamorphosis (Money et al., 1958, *Endocrinology* 63:20–28).

Based on these observations, it was conceived that as yet unidentified cellular responses may be altered or induced by certain diiodo thyronine analogues which do not exhibit either mode of action (metabolic or differentiating) exhibited by thyroxine T3 and T4.

The Diiodo Thyronine Analog Compounds

Diiodo thyronine analogues useful in the methods of the present invention are generally compounds having the structural formula:

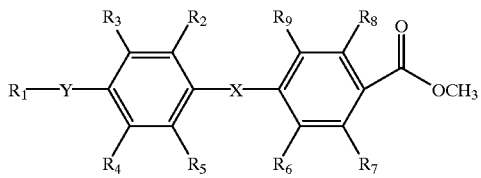

and pharmaceutically acceptable salts thereof, wherein:

X=O, S, $CH_2$, carboxy or absent;
Y=O or S;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen, and
$R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

In a preferred embodiment, diiodo thyronine analogues useful in the methods of the present invention are compounds having the structural formula:

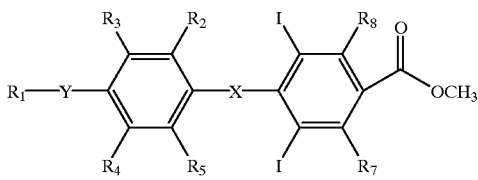

and pharmaceutically acceptable salts thereof, wherein:

X=O, S, $CH_2$, carboxy or absent;
Y=O or S;
$R_1$=methyl or ethyl;
$R_2$, $R_3$, $R_4$ and $R_5$ are each independently selected from the group consisting of: H, (C–$C_4$) alkyl, ($C_1$–$C_4$) alkenyl, ($C_1$–$C_4$) alkynyl, hydroxyl, ($C_1$–$C_4$) alkoxy and halogen; and
$R_7$ and $R_8$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$.

In a particularly preferred embodiment, the diiodo thyronine analogue is methyl 3,5-diiodo-4-(4'-methoxyphenoxy) benzoate ("DIME").

Also useful in the compositions and methods of the present invention are ketone diiodo thyronine analogues. Ketone diiodo thyronine analogues useful in the methods of the present invention are generally compounds having the structural formula:

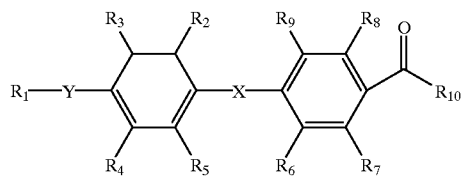

and pharmaceutically acceptable salts thereof, wherein:

X=O, S, $CH_2$, carboxy or absent;
Y=O or S;
$R_1$=methyl or ethyl;
$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkyl, hydroxyl, (($C_1$–$C_4$) alkoxy and halogen;
$R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$, and $NH_2$; and
$R_{10}$ is selected from the group consisting of ($C_1$–$C_4$) alkyl, ($C_1$–$C_4$) alkenyl, and ($C_1$–$C_4$) alkynyl.

In a preferred embodiment, compounds useful in the methods of the present invention are compounds having the structural formula:

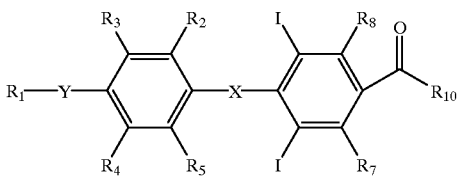

and pharmaceutically acceptable salts thereof, wherein:

X=O, S, CH$_2$, carboxy or absent;

Y=O or S;

R$_1$=methyl or ethyl;

R$_2$, R$_3$, R$_4$ and R, are each independently selected from the group consisting of: H, (C$_1$–C$_4$) alkyl, (C$_1$–C$_4$) alkenyl, (C,—C$_4$) alkynyl, hydroxyl, (C$_1$–C$_4$) alkoxy and halogen; R$_7$ and R$_8$ are each independently selected from the group consisting of: H. (C$_1$–C$_4$) alkyl, (C$_1$–C$_4$) alkenyl, (C$_1$–C$_4$) alkynyl, hydroxyl, (C$_1$–C$_4$) alkoxy, halogen, NO$_2$ and NH$_2$; and R$_{10}$ is selected from the group consisting of (C$_1$ to C$_4$) alkyl, (C$_1$–C$_4$) alkenyl and (C$_1$ to C$_4$) alkynyl.

In a particularly preferred embodiment, the compound is selected from the group consisting of 1-[3,5-diiodo-4-(4'-methoxyphenoxy)-phenyl]-ethanone (DIPE) and I-[3,5-diiodo-4-(4'-methoxyphenoxy)-phenyl]-1-propanone (DIPP).

Definitions:

"Alkyl" refers to a saturated branched, straight chain or cyclic hydrocarbon radical. Typical alkyl groups include methyl, ethyl, propyl, isopropyl, cyclopropyl, butyl, isobutyl, cyclobutyl, tert-butyl, pentyl, hexyl and the like.

"Alkenyl" refers to an unsaturated branched, straight chain or cyclic hydrocarbon radical having at least one carbon-carbon double bond. The radical may be in either the cis or trans conformation about the double bond(s). Typical alkenyl groups include ethenyl, propenyl, isopropenyl, cyclopropenyl, butenyl, isobutenyl, cyclobutenyl, tert-butenyl, pentenyl, hexenyl and the like.

"Alkynyl" refers to an unsaturated branched, straight chain or cyclic hydrocarbon radical having at least one carbon-carbon triple bond. Typical alkynyl groups include ethynyl, propynyl, butynyl, isobutynyl, pentynyl, hexynyl and the like.

"Alkoxy" refers to an —OR radical, where R is alkyl, alkenyl or alkynyl, as defined above.

"Halogen" generally refers to fluoro, chloro, bromo and iodo substituents. However, as used herein it preferably refers to iodo.

"Mammal" refers to animals or humans.

"Therapeutically effective amount" refers to an amount of a compound or composition effective to inhibit or prevent viral replication or result in amelioration of symptoms associated with viral diseases.

"Diiodo thyronine analog" as used herein refers to both the diiodo thyronine analogs defined herein and to the ketone analogs of the same defined herein. Specific exemplary diiodo thyronine analogs include DIME, DIPE and DIPP. The compounds included within the meaning of the term have structural similarity to thyroxine.

Diiodo thyronine analogues such as DIME have been described in the literature. However, unlike thyroxine, DIME was reported to have no significant metabolic or cell differentiating activity (as determined by tadpole metamorphosis) (Money et al., 1958, *Endocrinology* 63:20–28; Stasilli et al., 1959, *Endocrinology* 64:62–82). For example, uptake of iodine into the thyroid of rats is only marginally (15%) inhibited by DIME as compared to thyroxine (Money et al., 1959, *Endocrinology* 64:123–125). Furthermore, DIME was reported to have no inhibitory activity against the growth of a non-malignant mouse pituitary adenoma (Kumaoka et al., 1960, *Endocrinology* 66:32–38; Grinberg et al., 1962, *Cancer Research* 22:835–841).

It has now been discovered that certain diiodo thyronine analogues having no significant hormonal activity, particularly DIME, inhibit or prevent viral replication. These antiviral activities are sensitive to structure. Testing of thirteen structural analogues and homologues of DIME indicates that even minor alterations of the methyl ester and 4'-methyoxy substituents renders the molecule inactive. Whereas DIME is highly active both in cellular assays and in vivo, the 4'-propoxy and ethyl ester homologues are inactive. Accordingly, DIME defines a critical arrangement of molecular moieties, or a pharmacophore, having specific anti-viral activity and consequently significant therapeutic potential.

While not intending to be bound by theory, it is believed that the most probable molecular mode of action of the diiodo thyronine analogues described herein is disruption of microtubules. The mode of action of DIME in tumors was previously pinpointed to its selective permeation into tumor cells in vivo and its binding to cellular microtubules (Mendeleyev et al. *International J. of Oncology* 10:689–695 (1997); Zhen et al. *International J. of Oncology* 10:905–910 (1997); Buki et al. *International J. of Oncology* 10: 911–913 (1997), Buki et al. *International J. of Oncology* 11:1247–1250 (1997); Kirsten et al. *International J. of Oncology* 13:49–55 (1998) resulting in inhibition of tubulin polymerization. A DIME-tubulin association takes place already in anaphase (Buki et al. *International J. of Oncology* 11:1247–1250 (1997)) which disrupts the microtubule network. It is well established that a critical cellular function of microtubules, including associated proteins, is serving as reversible intracellular transporters (molecular motors) presumably from cytoplasmic to nuclear structures. This transport involves proteins and subcellular structures such as mitochondria and microsomes, etc. (Spudich, *Nature* 372:515–518 (1994); Howard, *Ann. Rev. Physiol.* 58:703–729 (1996); Case et al., *Cell* 90:959–966 (1977); Henningsen et al., *Nature* 389:93–95 (1997).

It was previously demonstrated that RT-generated provirus (from HIV or other retroviruses) also requires an ATP-dependent transport to the genomic DNA where integration of the proviral DNA takes place. This is an obligatory step necessary for viral replication. Disruption of the microtubular transport system by DIME prevents viral replication by the inhibition of the transport of proviral DNA to the integration site at the genomic DNA. This constitutes a novel antiviral chemotherapy wherein viral replication is blocked at a critical intracellular transport site. Since DIME does not act directly on the retrovirus, this chemotherapy sidesteps many complications of viral mutations, drug resistance development, etc. Furthermore disruption of microtubules by DIME induces apoptosis (Buki et al. *International J. of Oncology* 11:1247–1250 (1997)). Thus the virally infected cells are killed and the source of viral synthesis in the organism, i.e. sustained infection of the other cells, is eliminated.

While alterations at the ester and 4'-positions appear to significantly affect the effectivity of DIME, diiodo thyronine analogues useful for depressing viral replication and infection and treating viral infection in vivo are not limited to DIME. For example, the 4'-ethoxy homologue exhibits about 25–30% maximal cytocidal action on human cancer cells as compared to DIME. It is also expected that DIME may be substituted at the aromatic ring positions or bridge oxygen without significant loss of activity.

It is known that the aromatic rings of thyroxine are not contained within the same plane (Jorgensen, 1978, "Thyroid Hormones and Analogues II. Structure-Activity Relationships," In: *Hormonal Proteins and Peltides*, Vol. VI, pp. 107–204, C. H. Li, ea., Academic Press, NY). It is also known that the ring positions of both of the aromatic rings in thyroxine can be substituted with a variety of substituents, including alkyl, halogen, nitro and amino groups with varying degrees of retention of hormonal activity. Id. Furthermore, the ether oxygen connecting the rings can be absent or replaced with a variety of groups or atoms that do not confine the aromatic rings to the same plane, such as, for example, a methylene group, a carboxy group or sulfur, without significant loss of hormonal activity. Id. Accordingly, it is expected and predictable that similar substitutions on DIME will not effect significant loss of anti-cancer and anti-viral activity.

Significantly, the 2'-chloro analogue of DIME exhibited about 25% maximal inhibitory action on the growth of human cancer cells as compared to DIME in studies set forth in U.S. Ser. Nos. 08/655,267 and 08/833,272.

Due to the stringent correlation between in vitro and in vivo efficacy, effective compounds useful in the methods of the invention may be conveniently identified in in vitro assay screening tests. Such tests may screen for the ability of a particular compound to inhibit viral replication by inhibiting transport of proviral DNA to the integration site at the genomic DNA. Typically, compounds useful in the methods of the present invention will block viral replication at a critical intracellular transport site by a significant factor. Such tests may also screen for the ability of a particular compound to inhibit viral replication in vitro or in vivo or abolish pathology associated with virally-infected cells.

As will be appreciated by the skilled artisan, many particular viruses or varieties of virally-infected cell cultures and cell lines may be used to screen for activity. Of course, other in vitro and/or in vivo assays as will be apparent to the skilled artisan to screen for anti-viral activity may also be employed to identify effective diiodo thyronine analogues useful in the present invention.

The chemical formulae referred to herein may exhibit the phenomena of tautomerism or conformational isomerism. As the formulae drawings within this specification can only represent one of the possible tautomeric or conformational isomeric forms, it should be understood that the invention encompasses any tautomeric or conformational isomeric forms which exhibit biological or pharmacological activities similar to DIME, as described herein.

In addition to the above-described compounds and their pharmaceutically acceptable salts, the invention may employ, where applicable, solvated as well as unsolvated forms of the compounds (e.g. hydrated forms).

The compounds described herein may be prepared by any process known to be applicable to the preparation of chemical compounds. Suitable processes are illustrated by the representative examples. Necessary starting materials may be obtained by standard procedures of organic chemistry.

The Vinca Alkaloid Compounds

The methods and compositions of the present invention may feature a vinca alkaloid or a biologically active analog thereof. Several vinca alkaloids obtained from *Vinca rosea* have demonstrated efficacy in the treatment of malignancies. Some of these include leurosine (U.S. Pat. No. 3,370,057), vincaleukoblastine or vinblastine (U.S. Pat. No. 3,097,137), leuroformine (Belgian Pat. No. 811,110); leurosidine (vinrosidine) and leurocristine or vincristine (both in U.S. Pat. No. 3,205,220); deoxy vinblastine "A" and "B" *Tetrahedron Letters,* 783 (1958); 4-desacetoxyvinblastine (U.S. Pat. No. 3,954,773); 4-desacetoxy-3-hydroxyvinblastine (U.S. Pat. No. 3,944,554); leurocolombine (U.S. Pat. No. 3,890,325) and vincadioline (U.S. Pat. No. 3,887,565). At least two of these alkaloids, vinblastine and vincristine, are now marketed as drugs for treating malignancies, especially leukemias and related diseases in humans. Vincristine has usually been thought of as the most active and useful agent in the treatment of leukemias but is also the least abundant of the anti-neoplastic alkaloids of *Vinca rosea*. The two marketed alkaloids are customarily administered by the intravenous route.

Chemical modification of the vinca alkaloids has been relatively limited. Among the successful modifications of physiologically-active alkaloids has been the preparation of dihydro vinblastine (U.S. Pat. No. 3,352,868) and the replacement of the acetyl group at C-4 (carbon no. 4 of the vinblastine ring system) with higher alkanoyl group or with unrelated acyl groups. (U.S. Pat. No. 3,392,173). One of the derivatives in which a chloracetyl group replaced the C-4 acetyl group of vinblastine has been shown to be a useful intermediate for the preparation of structurally modified vinblastine compounds in which an N,N-dialkylglycyl group replaced the C-4 acetyl group of vinblastine (U.S. Pat. No. 3,387,001). C-3 carboxamide derivatives of vinblastine, vincristine, vincadioline etc. have also been prepared and found to be active anti-tumor agents. (Belgian Pat. No. 813,168.) Certain of the amide derivatives actually approach the activity of vincristine against these tumors. One of these amides, 4-desacetyl vinblastine C-3 carboxamide or vindesine has been found active in certain leukemias. In humans, vindesine appears to have less neurotoxicity than does vincristine.

Certain vinca alkaloid derivatives are described by, e.g. Miller et al., U.S. Pat. No. 4,160,767 and United States Reissue No. 30,561, the disclosures of which are herein incorporated by reference. Additional compounds featuring transferrin coupled to vinca alkaloids are disclosed by Ades et al., U.S. Pat. No. 4,522,750, and certain hydrazine succinimide derivatives of vinca alkaloids are disclosed by Cullinan et al., U.S. Pat. No. 4,667,030, the disclosures of which are herein incorporated by reference. Compounds which are functional analogs of naturally-occurring vinca alkaloids and which retain substantial antineoplastic and/or anti-viral and/or anti-inflammatory are specifically contemplated within the scope of this invention.

It has been shown experimentally that the vinca alkaloids like duiodo thyronine analogues bind to microtubules. The $K_D$ of DIME vs tubulin is in the order of $1-1.4 \times 10^{-5}$ M and that of vincristine may be a thousand-fold higher (*Microtubules*, Wiley-Liss Publications, John Wiley and Sons Inc., NY (1994)), consequently the two ligands may bind proportionally to cellular microtubules. However, the intracellular consequences of ligand-binding site interactions on microtubules may be quantitatively different for both drugs alone or in combination. For example the activation mechanisms of caspase 3, essential to induce apoptosis, could be cooperatively influenced by both ligands. It is presently unknown how microtubules may be involved in the regulation of apoptotic pathways. It has been reported that vinca alkaloids can activate the JNK pathway, MEKK1/SEK1 and c-Jun/AP-1 (Osborn et al. *Proc. Amer.*

Assoc. for Cancer Res. 177, Abstr. No. 1213 (1988)) reactions which lead to apoptosis, possibly via caspase 3. It has been reported that microtubule-reactive drugs, taxol and vinca alkaloids can activate both Ras and apoptosis-regulating kinases (ASK1), pathways (Wang et al. *J. Biol. Chem.* 273: 4928–4936, (1998)) presumably leading to Bcl-2-regulated apoptosis.

One problem associated with many vinca alkaloid compounds in the methods of the present invention is that they are not selectively toxic for virally infected cells. However, particular vinca alkaloids that demonstrate only a substantial toxicity for cells infected by the target virus are particularly useful within the scope of the present invention.

Other Microtubule-binding compounds

Any compound capable of inhibiting microtubule formation, tubulin polymerization or proper functioning of microtubules is intended within the scope of the present claims. The crucial function of the compounds intended within in the scope of the present invention is that they function to inhibit or prevent transport of viral genetic material into the nucleus of the host cell. Binding microtubules may alone be sufficient to prevent such transport. Inhibiting microtubule formation and inhibiting tubulin polymerization may also prevent such transport. Preferably, the compounds of the present invention will be selectively permeable for the cells infected by the target virus. That is, the preferred compounds according to the present invention will not be substantially toxic to uninfected cells. Compounds that may fit this criteria in some circumstances include, e.g. taxol.

Viruses

The compositions comprising compounds capable of binding microtubules, inhibiting microtubule formation or inhibiting polymerization of tubulin such as the diiodo thyronine analogues described herein are useful for treating a wide variety of viruses. Such viruses include, by way of example and not limitation, human immunodeficiency virus (HIV), herpes simplex viruses (HSV), hepatitis viruses, influenza viruses, papillomaviruses, cytomegalovirus (CMV), respiratory syncytial virus (RSV), etc.

In a preferred embodiment of the invention, the virus is a retrovirus, and in especially preferred embodiments, the virus is HIV.

Pharmaceutical Formulations and Routes of Administration

The compounds capable of binding microtubules, inhibiting microtubule formation or inhibiting tubulin polymerization according to the present invention, such as diiodo thyronine analogues, can be administered to a human patient in the form of a pharmaceutically acceptable salt, or in the form of a pharmaceutical composition where the compound is mixed with suitable carriers or excipient(s) in a therapeutically effective amount, i.e., at doses effective to depress or suppress viral replication or result in amelioration of symptoms associated with viral diseases.

Routes of Administration

The pharmaceutical compositions described herein may be administered by a variety of routes. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Furthermore, one may administer the compounds in a targeted drug delivery system, for example, in a liposome coated with tumor-specific antibody. The liposomes will be targeted to and taken up selectively by the tumor.

In a preferred embodiment, the diiodo thyronine analogues and pharmaceutical compositions described herein are administered orally.

Composition/Formulation

The pharmaceutical compositions described herein may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manners using one or more physiologically acceptable carriers comprising excipients and auxiliaries that facilitate processing of the active compounds into preparations which can be used pharmaceutically. Proper formulation is dependent upon the route of administration chosen.

For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insulator may be formulated containing a powder mix of the compound and a suitable powder base such as lactose or starch.

The compounds may be formulated for parenteral administration by injection, e.g., by bolus injection or continuous infusion. The compositions may take such forms as suspensions, solutions or emulsions in oily or aqueous vehicles, and may contain formulatory agents such as suspending, stabilizing and/or dispersing agents.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A suitable pharmaceutical carrier for hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Other formulations suitable for administering the diiodo thyronine analogues described herein will be apparent to those having skill in the art, and may be found, for example, in *Remington's Pharmaceutical Sciences*, Mack Publishing Co., Easton, Pa., latest edition.

Effective Dosages

Pharmaceutical compositions suitable for use in the present invention include compositions wherein the active ingredients are contained in a therapeutically effective amount. Determination of an effective amount is well within the capability of those skilled in the art, especially in light of the detailed disclosure provided herein.

Initial dosages can also be estimated from in vivo data. Studies have shown that DIME has a half-life ($t_o$,) in serum of about 4 hours, and is 87% bioavailable by per os administration. One having ordinary skill in the art could readily optimize administration to humans based on this data. Dosage amount and interval may be adjusted individually to provide optimal results.

In cases of selective uptake by virally-infected cells, the effective concentration of the drug may not be related to plasma concentration. One having skill in the art will be able to optimize therapeutically effective local dosages without undue experimentation.

The amount of composition administered will, of course, be dependent on the subject being treated, on the subject's weight, the severity of the affliction, the manner of administration and the judgment of the prescribing physician.

Treatment may be repeated intermittently while viral infections are detectable or even when they are not detectable. Due to the apparent nontoxicity of the preferred compounds used in the present invention, the therapy may be provided alone or in combination with other anti-cancer or other drugs, such as for example AZT, anti-inflammatories, antibiotics, corticosteroids, vitamins and the like.

Toxicity

Toxicity and therapeutic efficacy of the compounds described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. The exact formulation, route of administration and dosage can be chosen by the individual physician in view of the patient's condition. (See, e.g., Ansel et al., 1995, *Pharmaceutical Dosage Forms and Drug Delivery Systems*, $6^{th}$ ed.).

One of the advantages, among others, of using the diiodo thyronine analogues described herein to treat viral infections is their lack of toxicity. For example, it has been found that a daily oral dose of 1 g/kg administered for 12–15 days produced no ill effects in nude mice. Since the i.v. serum half-life ($t_{1/2}$) of DIME is about 4 hours, repeated daily dosages of the diiodo thyronine analogues described herein without ill effects is predictable. However, those of skill in the art may easily determine other substantially non-toxic compounds within the scope of the present invention without undue experimentation.

EXAMPLES OF THE PREFERRED EMBODIMENTS

The following examples serve to illustrate the invention. They are not intended to be limiting, and those skilled in the art will readily understand that the invention is limited only by the appended claims.

Example 1

Synthesis of Diiodo thyronine Analogues

The following examples serve to illustrate the invention. They should not be construed as narrowing it, or limiting its scope.

Fourteen diiodo thyronine analogues were synthesized, purified and characterized. A summary of the structure of each synthesized compound and select physical data is provided at 5 Table 1, below.

TABLE 1

Diiodo thyronine Analogues Synthesized

| No. | $R_1$ | $R_2$ | $R_3$ | $R_4$ | m.p. (° C.) | Formula | Mass (calcd.) | Mass (found) |
|---|---|---|---|---|---|---|---|---|
| 1 | $CH_3O$ | $CH_3O$ | H | H | 153–155 | $C_{15}H_{12}I_2O_4$ | 509.882513 | 509.882960 |
| 2 | EtO | $CH_3O$ | H | H | 123–125 | $C_{16}H_{14}I_2O_4$ | 523.898163 | 523.898737 |
| 3 | n-PrO | $CH_3O$ | H | H | 114–116 | $C_{17}H_{16}I_2O_4$ | 537.913813 | 537.914014 |
| 4 | n-BuO | $CH_3O$ | H | H | 82–84 | $C_{18}H_{18}I_2O_4$ | 551.929463 | 551.930000 |
| 5 | $CH_3O$ | EtO | H | H | 96–98 | $C_{16}H_{14}I_2O_4$ | 523.898163 | 523.898202 |
| 6 | $CH_3O$ | HO | H | H | 233–235 | $C_{14}H_{10}I_2O_4$ | ref[a] | |
| 7 | $CH_3O$ | $H_2N$ | H | H | 207–209 | $C_{14}H_{11}I_2NO_3$ | 494.882847 | 494.881880 |
| 8 | $CH_3O$ | $(CH_3)HN$ | H | H | 181–183 | $C_{15}H_{13}I_2NO_3$ | 508.898497 | 508.898971 |
| 9 | $CH_3O$ | $(CH_3)_2N$ | H | H | 162–164 | $C_{16}H_{15}I_2NO_3$ | 522.914148 | 522.914364 |
| 10 | HO | $CH_3O$ | H | H | 204 (dec.)[b] | $C_{14}H_{10}I_2O_4$ | 495.866863 | 495.867453 |
| 11 | H | $CH_3O$ | H | H | 142–144 | $C_{14}H_{10}I_2O_3$ | 479.871948 | 479.872553 |
| 12 | I | $CH_3O$ | H | H | 139–141 | $C_{14}H_9I_3O_3$ | 605.768600 | 605.767839 |
| 13 | H | $CH_3O$ | H | $CH_3O$ | 123–125 | $C_{15}H_{12}I_2O_4$ | 509.882513 | 509.882387 |
| 14 | $CH_3O$ | $CH_3O$ | Cl | H | 132–134 | $C_{15}H_{11}ClI_2O_4$ | 543.843541 | 543.843424 | ref[a]: Compound 6 was prepared according to Borrows et al., J. Chem. Soc. 1949:S185–S190.
[b]: Decomposition temperature.

1.1 Methyl 3,5-diiodo-4-(4'methoxyphenoxy) benzoate Compound 1)

Methyl 3,5-diiodo-4-(4'-methoxyphenoxy)benzoate (Compound 1) was prepared as described in Borrows et al., 1949, *J. Chem. Soc.* 1949(Supp. Issue No. 1):S185–S190, and recrystallized from 95% ethanol. Melting point: 153–155° C.

Mass spectrum: FAB, m/z (relative intensity): 510 (M+, 100), 479 (4.5), 384 (4.5). High-resolution data for the M+ peak: calculated for $C_{15}H_{12}I_2O_4$, 509.882513; found, 509.882960 (deviation=−0.9 ppm).

$^1$H NMR spectrum in DMSO-$d_6$ (s (ppm) values relative to TMS): 3.719 (3H, singlet), 3.876 (3H, singlet), 6.693 (2H, doublet, J=9.45 Hz, plus fine-splitting), 6.845 (2H, doublet, H=9.36 Hz, plus fine-splitting), 8.390 (2H, singlet).

1.2 Methyl 3,5-diiodo-4-(4'-ethoxyphenoxy) benzoate (Compound 2)

Methyl 3,5-diiodo-4-(4'-ethoxyphenoxy) benzoate (Compound 2) was synthesized using the general methodology of Borrows, et al., supra.

1.2.1 Methyl 3,5-dinitro-4-(4'-ethoxphenoxy) benzoate

In a 50-ml flask at ambient temperature 4-ethoxy-phenol (Aldrich) (1492 mg, 10.8 mmoles) was stirred with 2.0 M aqueous KOH (5.50 ml) to form potassium 4-ethoxyphenolate. Methyl 4-chloro-3,5-dinitrobenzoate (Ullmann, 1909, *Annalen der Chemie* 366:92–93; commercial source: Spectrum Chemical Company, Gardena, Calif.; 2606 mg, 10.0 mmoles) was added, the mixture heated to reflux for 1 hour and chilled in an ice-bath, whereupon a rubbery mass of product deposited. Cold aqueous 1.0 M KOH (20 ml) was added, and 35 upon continued chilling the product solidified. The yellow-orange solid was broken-up, collected on a suction filter, rinsed with water and dried. The material (3.08 g) was crystallized from hot 95% ethanol (50 ml) to give 2.56 g (70.6% yield) of methyl 3,5-dinitro-4-(4'-ethoxyphenoxy)benzoate. Melting point: 101–103° C.

Mass spectrum (El): M+ in high-resolution: calculated for $C_{16}H_{14}N_2O_7$: 362.075016; found, 362.074793 (deviation=0.65 ppm).

1.2.2 Methyl 3 5-diiodo-4(4'-ethoxyphenoxy)benzoate

A portion (724.4 mg, 2.00 mmoles) of methyl 3,5-dinitro-4-(4'-ethoxyphenoxy)benzoate was dissolved in glacial acetic acid (50 ml), mixed with 10% palladium-on-carbon catalyst (Aldrich) (200 mg) in a Parr Model 4561 Mini-Reactor, charged with an atmosphere of $H_2$ (43 15 psi) and rapidly stirred at ambient temperature until the pressure-drop due to the reaction ceased (6 minutes, 16 psi final). The mixture was immediately filtered through a bed of celite to remove the catalyst and stripped of acetic acid solvent on a rotary evaporator to yield a brown, oily residue representing the crude 3,5-diamine derivative. The crude diamine was dissolved in glacial acetic acid (6.0 ml) and tetrazotized by adding it dropwise over a period of 3 minutes to a stirred, ice-cold solution of sodium nitrite (345 mg, 5 mmoles) in concentrated sulfuric acid (3.5 ml). After stirring for 30 minutes at ice-bath temperature, the viscous mixture was pipetted into a rapidly stirred solution of potassium iodide (3.0 g) in distilled water (2.5 ml) at ambient temperature. The dark mixture was stirred for 30 minutes and finally heated to 70° C. for 5 minutes. The mixture was poured into ethyl acetate (100 ml) and water (50 ml) was added. The two-phase mixture was transferred to a separatory funnel, additional ethyl acetate (50 ml) and water (50 ml) added, and the product extracted into the ethyl acetate. The organic (ethyl acetate) layer was washed with 35 two additional portions of water (50 ml each) and dried over anhydrous sodium sulfate. Subsequent removal of ethyl acetate by evaporation yielded a dark, tarry residue.

This crude product was dissolved in acetone (8 ml) and purified by preparative thin-layer chromatography plates (five) (Whatman, silica-gel, 1000-m layer, 20 cm×20 cm, with fluorescent indicator). The plates were developed in n-hexane: ethyl acetate: acetic acid (3:1:0.8 v/v/v). The product band (Rf=0.84), visualized under UV light, was collected from the respective plates, pooled, and eluted from the silica-gel (held in a sintered glass funnel) with ethyl acetate (3×50 ml). Removal of ethyl acetate yielded an off-white solid that was crystallized from 95% ethanol (10 ml). Yield: 275 mg total of two crops of white crystals (26% based on 2 mmoles of the dinitro precursor). Melting point: 123–125° C.

Mass spectrum: EI, m/z (relative intensity): 524 (M+, 100), 496 (16.7), 310 (9.1), 242 (6.1), 211 (7.6), 155 (6.1). High-resolution data for the M+ peak: calculated for C16H14I2O4: 523.898163; found, 523.898737 (deviation=−1.1 ppm).

$^1$H NMR spectrum in DMSO-d6 (S (ppm) values relative to TMS): 1.303 (3Hl, triplet, J=6.94 Hz), 3.877 (3H, singlet), 3.971 (2H, quartet, J=6.95 Hz), 6.678 (2H, doublet, J=8.98 Hz, plus fine-splitting), 6.879 (2H, doublet, J=9.06 Hz, plus fine-splitting), 8.389 (211, singlet).

1.3 Methyl 3,5-diiodo-4-(4'-n-propoxvphenoxy)benzoate (Compound 3)

Methyl 3,5-diiodo-4-(4'-n-propoxyphenoxy)benzoate (Compound 3) was prepared as described in Example 1.2. The dinitro precursor was synthesized by treating an aqueous solution of potassium 4-n-propoxy-phenolate (prepared from commercial 4-n-propoxy-phenol) with methyl 4-chloro-3,5-dinitrobenzoate. The dinitro product was reduced by $H_2$/Pd(C) to the diamine derivative, which was then tetrazotized with $NaNO_2/H_2SO_4$ and converted to the diiodo product by reaction with potassium iodide (Sandmeyer reaction). Purification was by preparative TLC and crystallization.

1.4 Methyl 3 5-diiodo-4-(4'-n-butoxvphenoxy) benzoate (Compound 4)

Methyl 3,5-diiodo-4-(4'-n-butoxyphenoxy)benzoate (Compound 4) was prepared as described in Example 1.2. The dinitro precursor was synthesized by treating an aqueous solution of potassium 4-n-butoxyphenolate (prepared from commercial 4-n-butoxyphenol) with methyl 4-chloro-3,5dinitrobenzoate. The dinitro product was reduced by $H_2$/Pd(C) to the diamine derivative, which was then tetrazotized with $NaNO_2/H_2SO_4$ and converted to the diiodo product by reaction with potassium iodide (Sandmeyer reaction). Purification was by preparative TLC and crystallization.

1.5 Ethyl 3,5-diiodo-4-(4'-methoxvphenoxv) benzoate (Compound 5)

Ethyl 3,5-diiodo-4-(4'-methoxyphenoxy)benzoate (Compound 5) was synthesized by way of 3,5-diiodo-4-(4'-20 methoxyphenoxy) benzoyl chloride, the latter having been described in Borrows et al., supra. Thus, in a 10 ml flask 3,5-diiodo-4-(4'-methoxyphenoxy)benzoic acid (99.2 mg, 0.200 mmole) was converted to 3,5-diiodo-4-(4'-methoxyphenoxy) benzoyl chloride. After removal of excess thionyl chloride under vacuum, anhydrous ethanol (5.0 ml) was added with stirring and the mixture heated to 70° C. for 5 minutes. Excess ethanol was removed and the dry residue dissolved in hot 95% ethanol (4.0 ml), from which the product ester crystallized in the refrigerator (3° C.). Yield: 55.8 mg (53%) of buff-colored crystals. Melting point: 96–98° C.

Mass spectrum (EI): High-resolution data for the M+ peak: calculated for $C_{16}H_{14}I_2O_4$, 523.898163; found, 523.898202 (deviation=−0.1 ppm).

$^1$H NMR spectrum in DMSO-d6 (6 (ppm) values relative to TMS): 1.336 (3H, triplet, J=7.19 Hz), 3.717 (3H, singlet), 4.336 (2H, quartet, J=7.06 Hz), 6.695 (2lI, doublet, J=9.34 Hz, plus fine-splitting), 6.895 (2H, doublet, J=9.20, plus fine-splitting), 8.389 (2H, singlet).

1.6 3.5-diiodo-4-(4'-methoxvphenoxy)benzoic acid (Compound 6)

3,5-diiodo-4-(4'-methoxyphenoxy)benzoic acid (Compound 6) was synthesized as described in Borrows et al., supra.

1.7 3,5-diiodo-4-(4'-methoxyphenoxy)benzamide (Compound 7)

3,5-diiodo-4-(4'-methoxyphenoxy)benzamide (Compound 7) was synthesized by amidating Compound 1. In a 125 ml flask, methyl 3,5-diiodo-4-(4'-methoxyphenoxy) benzoate (Compound 1) (100 mg, 0.196 mmole) was dissolved in anhydrous methanol (60 ml). Anhydrous ammonia gas was bubbled into the solution for 5 minutes at a moderate rate at ambient temperature. After standing for 1 hour in the stoppered flask, the ammonia gas treatment was repeated (5 minutes) and the mixture allow to stand in the stoppered flask for 48 hours. The methanol/ammonia was removed by rotary evaporation, the dry residue dissolved in methanol: wafer (7:3 v/v) (30 ml) and crystallized in the refrigerator (3° C.). Yield: 58.3 mg (60% yield) of buff-colored crystals. Melting point: 207–209° C.

Mass spectrum (FAB): High-resolution data for the M+peak: calculated for $C_{14}H_{11}I_2NO_3$, 494.882847; found, 494.881880 (deviation=2.0 ppm).

$^1$H NMR spectrum in DMSO-$d_6$ (6 (ppm) values relative to TMS): 3.716 (3H, singlet), 6.682 (2H, doublet, J=8.93 Hz), 6.895 (2H, doublet, J=8.99 Hz), 7.528 (1H, singlet), 8.113 (1H, singlet), 8.402 (2H, singlet).

1.8 5-diiodo-4-(4'-methoxy phenoxy)-N-methyl benzamide (Compound 8)

3,5-diiodo-4-(4'-methoxyphenoxy)-N-methyl benzamide (Compound 8) was prepared by way of 3,5-diiodo-4-(4'-methoxyphenoxy)benzoyl chloride (see, Example 1.5). The acid chloride was reacted with excess methylamine in tetrahydrofuran at ambient temperature (1 hour), filtered to remove methylamine-hydrochloride precipitate, the solvent evaporated and the product crystallized from 95% ethanol.

1.9 3,5-diiodo-4-(4'-methoxy phenoxy)-N N-dimethyl benzamide (Compound 9)

3,5-diiodo-4-(4'-methoxyphenoxy)-N,N-dimethyl benzamide (Compound 9) was prepared way of 3,5-diiodo-4-(4'-methoxyphenoxy)benzoyl chloride (see, Example 1.5). The acid chloride was reacted with excess dimethylamine in tetrahydrofuran at ambient temperature (1 hour), filtered to remove dimethylamine-hydrochloride precipitate, the solvent evaporated and the product crystallized from absolute ethanol.

1.10 Methyl 3,5-diiodo-4-(4'-hydroxyphenoxy) benzoate (Compound 10)

Methyl 3,5-diiodo-4-(4'-hydroxyphenoxy) benzoate (Compound 10) was prepared as described in Example 1.2. The dinitro precursor was prepared by reacting 4-chloro-3, 5-25 dinitrobenzoate with hydroquinone in pyridine solution as described in Borrows et al., supra.

1.11 Methyl 3.5-diiodo-4-phenoxybenzoate (Compound 11)

Methyl 3,5-diiodo-4-phenoxybenzoate (Compound 11) was prepared as described in Example 1.2. The dinitro 35 precursor was synthesized by treating an aqueous solution of potassium phenolate (prepared from commercial phenol) with methyl 4-chloro-3,5-dinitrobenzoate. The dinitro product was reduced by $H_2$/Pd(C) to the diamine derivative' which was then tetrazotized with $NaNO_2/H_2SO_4$ and converted to the diiodo product by reaction with potassium iodide (Sandmeyer reaction). Purification was by preparative TLC and crystallization.

1.12 Methyl 3,5-diiodo-4-(4'-iodophenoxy)benzoate (Compound 12)

Methyl 3,5-diiodo-4-(4'-iodophenoxy)benzoate (Compound 12) was synthesized as described in Example 1.2. Since the iodo-substituent in the dinitro precursor is itself labile with respect to reduction by $H_2$/Pd(C), the iodo-dinitro precursor was reduced to the iodo-diamine with iron powder in acetic acid/95% ethanol (see, e.g., Gemmill et al., 1956, J. Am. Chem. Soc. 78:2434–2436). The iododiamine was then tetrazotized and converted to the triiodo product using the Sandmeyer reaction. After purification by preparative TLC, the product (m.p. 139–141° C.) was crystallized from ethanol.

Mass spectrum (EI): High resolution data for the M+peak: calculated for C14H,O3I3, 605.768600; found, 605.767839 (deviation=1.3 ppm).

$^1$H NMR spectrum in DMSO-d6 (6 (ppm) values relative to TMS): 3.879 (3H, singlet), 6.628 (2H, doublet, J=8.97 Hz plus fine-splitting), 7.670 (2H, doublet, J=9.12 Hz plus fine-splitting), 8.396 (2H, singlet).

1.13 Methyl 3.5-diiodo-4-(3'-methoxy phenoxy benzoate (Compound 13)

Methyl 3,5-diiodo-4-(3'-methoxyphenoxy)benzoate (Compound 13) was synthesized as described in Example 1.2. The dinitro precursor was synthesized by treating an aqueous solution of potassium 3-methoxy phenolate (prepared from commercial 3-methoxyphenol) with methyl 4-chloro-3,5-dinitrobenzoate. The dinitro product was reduced by $H_2$/Pd(C) to the diamine derivative, which was then tetrazotized with $NaNO_2$/$H_2SO_4$ and converted to the diiodo product by reaction with potassium iodide (Sandmeyer reaction). Purification was by preparative TLC and crystallization.

1.14 Methyl 3 5-diiodo-4-(2'-chloro-4'-methoxy phenoxy)benzoate (Compound 14)

Methyl 3,5-diiodo-4-(2'-chloro-4'methoxyphenoxy)benzoate (Compound 14) was synthesized by the general methodology described in Example 1.2, but with an alternate method for the reduction of the dinitro precursor.

1.14.1 Methyl 3,5-dinitro-4-(2'-chloro-4'-methoxy phenoxy)benzoate

The dinitro precursor was prepared by reacting 2-chloro-4-methoxyphenol (Aldrich Chemical Co., Milwaukee, Wis.) as the potassium 2-chloro-4-methoxyphenolate with methyl 4-chloro-3,5-dinitrobenzoate, as described in Example 1.2.1.

The methyl 3,5-dinitro-4-(2'-chloro-4'-methoxyphenoxy)benzoate product (66% yield) was crystallized from ethanol to give orange crystals. Melting point: 116–119° C.

Mass Spectrum (EI): M+ in high resolution: calculated for C1sH11c1N2o8, 382.020393; found, 382.020187 (deviation=0.5 2 ppm).

1.14.2 Methyl 3,5-diiodo-4-(2'-chloro-4'-methoxy phenoxy)benzoate

Since the 2'-chloro substituent in the 25 dinitro precursor is labile with respect to reduction by $H_2$/Pd(C), the precursor was reduced to the 2'-chloro diamine with iron powder in acetic acid/95% ethanol, similarly to Example 1.12. Thus, in a 250 ml flask methyl 3,5-dinitro-4(2'-chloro-4'-methoxyphenoxy)benzoate (765.5 mg, 2.00 mmol) 30 was dissolved in glacial acetic acid (35 mL) and 95% ethanol (35 mL), the solution heated to 70° C. and iron powder added (2.00 g). The mixture was vigorously swirled in a heating bath (70° C.). After 3 min. of swirling, the mixture developed a brown color. Swirling was continued at 70° C. for 35 min. The mixture was then transferred to a separatory funnel, water (250 mL) and ethyl acetate (250 mL) were added, the product extracted into the ethyl acetate layer, and the ethyl acetate phase allowed to separate from the aqueous phase (3 hours). The extract was dried over anhydrous $Na_2SO_4$, filtered and the ethyl acetate removed by rotary evaporation to yield the crude 3,5-diamino product, which solidified.

The crude diamino product was immediately dissolved in glacial acetic acid (6.0 mL), tetrazotized and converted via the Sandmeyer reaction to methyl 3,5-diiodo-4-(2'-chloro-4'methoxyphenoxy)benzoate as described in Example 1.2. After purification by preparative thin layer chromatography (Rf=0.70) as described in Example 1.2, the product was crystallized from 95% ethanol (250.8 mg off-white crystals, 23% yield). Melting point: 132–134° C.

Mass spectrum: EI, m/z (relative intensity): 546 (34), 545 (16), 544 (M+, 100), 418 (6), 382 (6). High resolution data for the M+peak: calculated for C1sH11C1I2O4, 543.843541; found, 543.843424 (deviation=0.2 ppm).

$^1$H NMR spectrum in DMSO-D6 (S (ppm) values relative to TMS): 3.747 (3H, singlet), 3.881 (3H, singlet), 6.328 (1H, doublet, J=8.97 Hz), 6.780 (1H, doublet of doublets, J=9.10 Hz and J=2.95 Hz), 7.195 (1H, doublet, J=3.02 Hz), 8.400 (2H, singlet).

1.15 Other Compounds

Additional diiodo thyronine analogues described herein can be synthesized using the above-described syntheses from appropriate starting materials, as will be readily apparent to those having skill in the art of organic chemistry. Additional guidance can be found in the art, particularly in Borrows et al., supra; Clayton et al., 1951, *J. Chem. Soc.* 1951:2467–2473; Gemmill et al., 1956, *J. Am. Chem. Soc.* 78:2434–2436; Meltzer et al., 1957, *J. Orq. Chem.* 22:1577–1581; Crowder et al., 1958, *J. Chem. Soc.* 1958:2142–2149; Jorgensen, 1978, "Thyroid Hormones and Analogues, I. Synthesis, Physical Properties and Theoretical Calculations" In: *Hormonal Proteins and Peptides* Vol. VI, pp. 57–105, C. H. Li, Ed., Academic Press, NY (and references cited therein); and Jorgensen, 1978, "Thyroid Hormones and Analogues, II. Structure-Activity Relationships," In: *Hormonal Proteins and Peptides*, Vol. VI, pp. 107–204, C. H. Li, Ed., Academic Press, NY (and references cited therein).

Example 2
In vivo experiments using diiodo thyronine analogues

The following examples demonstrate the non-toxicity, bioavailability, serum half-life (tx) and in vivo efficacy of DIME in treating human mammary cancer xenografts in mice.

Toxicity

Ten nude mice were administered a daily oral dose of $^{14}$C-labeled DIME (Compound 1) (1.0 g/kg, 0.1 ml, in corn oil) for a period of 12–15 days. No ill effects were observed in any of the mice during the entire time of treatment.

Serum Half-Life (t½) and Bioavailability

Mice were orally dosed with 126 mg/kg 14C-labeled DIME (Compound 1). After dosing, blood sampling times were 15 and 30 minutes and 1, 2, 4, 6, 8 and 24 hours. Aliquots (50 μL) of blood were assayed in a liquid scintillation counter and data expressed as microgram-equivalents per mL.

The blood level data were analyzed by the RSTRIP method (Micromath, Salt Lake City, Utah). Parallel groups of mice were dosed intravenously with 24.5 mg/kg 14C-labeled DIME and blood sampling times were 10, 20 and 30 minutes and 1, 2, 4, 6 and 8 hours. The compound was determined to demonstrate about 85–90% bioavailability.

Results

The blood serum levels of $^{14}$C-labeled DIME (mg-eq./mL) were compared. The area under the blood concentration-time curve was 665.28 μg-hr./mL for the oral route (data represented by circles) and 156 μg-hr/mL for the intravenous route (data represented by squares). Bioavailability of orally administered DIME was calculated to be 83% from these data using a standard ratio×dose method. DIME half-life (t½) was about 2–2.5 hours.

In Vivo Efficacy

The ability of human tumors to grow as xenografts in athymic mice (e.g., nude mice) provides a useful in vivo model for studying the biological response to therapies for human tumors. Since the first successful xenotransplantation of human tumors into athymic mice (Rygaard et al., 1969, *Acta Pathol. Microbial. Scand.* 77:758–760), many different human tumor cell lines (e.g., mammary, lung, genitourinary, gastrointestinal, head and neck, glioblastoma, bone and malignant melanomas) have been successfully transplanted and grown into nude mice. Human mammary tumor cell lines, including MCF-7, ZR75-1 and MDA-MB-23 1, have been established as subcutaneous grafts in nude mice (Warri et al., 1991, *Intl. J. Cancer* 49:616–23; Ozzello et al., 1980, *Eur. J. Cancer* 16:553–559; Osbourne et al., 1985, *Cancer Res.* 45:584–590; Siebert et al., 1983, *Cancer Res.* 43:2223–2239).

This experiment demonstrates inhibition of MDA-MB-231 xenografts in nude mice.

Experimental Protocol MDA-MB-231 (human mammary cancer) cells were obtained from American Type Culture Collection (Rockville, Md.) and maintained in the recommended growth media. Twenty nude mice were each inoculated subcutaneously with MDA-MB-231 cells (106 cells/ 100 pL). To one group of ten mice, DIME was administered by gavage (250 mg/kg, 10 mL/kg in corn oil) once 5 per day, 5 days per week, for a total of 32 days. The other (control) group of ten mice was given administered vehicle only according to the same dosing schedule. Tumors were measured twice weekly using a Vernier caliper, and the mean tumor volume was determined at each time point. Comparisons between groups were made using an unpaired, two-tailed t-test and the results were analyzed using analysis of variance.

Results

The average tumor mass at days 14, 21, 28 and 32 post-inoculation for treated and untreated mice is tabulated in Table 2.

Results shown here demonstrate that 2 to 10 $\mu$M DIME inhibits HIV replication in infected human white cells. In addition, normal or stimulated white cells do not take up significant quantities of DIME, but HIV infected cells show significant drug uptake, similar to cancer cells. These two criteria identify DIME as a novel anti-HIV drug candidate and further identify the microtubule system as a target for intervention by other drugs targeting viruses.

Experimental Protocol

Lymphocytes were obtained from the Sacramento Blood Bank. After stimulation of cells with phytohaemagglutinine for 3 days, cells were exposed to varying concentrations of DIME (see abscissa of FIG. 1) and incubated for 2 hours at 37° C., 5% $CO_2$, followed by the addition of $3.2 \times 10^5$ $TCID_{50}$ HIV-1 viruses (strains HIV-, 89.6 and HIV-1 SF162). Viral growth was allowed to proceed for 3 days. HIV quantitation was performed by RT (reverse transcriptase) assays as reported (Torres et al., *AID Research and Human Refroviruses* 9:423–428 (1993). RT activity is shown in FIG. 1 as cpm (ordinate). It is apparent that RT, a quantitative measure of HIV replication in the supernatant, progressively diminishes as a function of DIME concentration.

Comparison with Nocodazole

Nocodazole is a well known antitubulin drug. It is highly toxic. Thus, we established a concentration that is relatively harmless to human white cells, i.e. between 0.1 and 1 $\mu$M. At 0.1 IM , nocodazole depressed HIV production by 40% thereby simulating the action of DIME. However DIME is completely nontoxic up to about 320 $\mu$M. Thus, its therapeutic usefulness is superior to that of nocodazole.

Intracellular DIME analysis in human lymphocytes was performed as described (Mendeleyev et al., *Intl. J. Oncol.* 10:689–695 (1997)) with the aid of $^{14}$C-DIME. After exposure of lymphocytes to varying concentrations of $^{14}$C-DIME, cells were centrifuged through di-n-butyl phthalate/ dinonylphthalate and separated cell pellets were dissolved in 0.3 M NaOH and counted. Cell volume was determined as

TABLE 2

MDA-MB-231 Tumor Volume After DIME Treatment

| Treatment group | Day 14 ± SEM[a] (p value) | Day 21 ± SEM[a] (p value) | Day 28 ± SEM[a] (p value) | Day 32 ± SEM[a] (p value) |
|---|---|---|---|---|
| Control (vehicle) | 284.6 ± 42.0 | 622.2 ± 58.1 | 979.0 ± 154 | 1176.6 ± 222.4 |
| DIME (250 MG/KG) | 172.0 ± 34.3 (p = 0.06) | 285.7 ± 62.4 (p = 0.02) | 430 ± 85.6 (p = 0.01) | 543.8 ± 122.1 (p = 0.01) |
| % decrease | 40% | 54% | 56% | 54% |

[a]SEM = standard error of the mean

These data indicate that DIME effects significant reduction of malignant tumor growth, even under a non-optimized treatment regimen.

In vivo Efficacy

Other diiodo thyronine analogues described herein are tested as described above. The analogues are expected to exhibit activity according to these assays.

Example 3

Inhibition of HIV replication in human white cells by DIME

The following data demonstrate that a hormonally inactive diiodothyronine derivative, DIME, is active in preventing or inhibiting viral replication.

reported (Gewert et al. *Eur. J. Biochem.* 116:487–494 (1981)). Both unstimulated and stimulated lymphocytes demonstrated negligible DIME uptake at 2.5 and 10 $\mu$M extracellular DIME concentrations over 6 hours whereas HIV harboring cells exhibited up to 10-fold accumulation of DIME over extracellular concentrations. These results are similar to those reported for DIME uptake into tumor cells (Mendeleyev et al., *Intl. J. Oncol.* 10:689–695 (1997)).

DIME inhibits HIV replication in human lymphocytes at the same concentration as it disrupts microtubules in tumor cells. The absence of toxicity predicts clinical usefulness of DIME for AIDS treatment. Furthermore, since influenza, hepatitis, herpes and papilloma viruses exhibit similar replication to HIV, DIME will be effective against these viruses as well.

Although the invention has been described with reference to the presently preferred embodiments, it should be understood that various modifications can be made without departing from the spirit of the invention. Accordingly, the invention is limited only by the following claims.

What is claimed is:

1. A method of treating a viral infection in a mammal needing such treatment comprising the step of administering a pharmaceutically effective amount of a compound having no significant hormonal activity capable of binding microtubules or inhibiting microtubule formation or inhibiting tubulin polymerization wherein said compound has the formula:

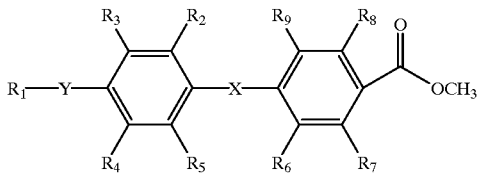

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy and halogen: and
$R_6$, $R_7$, $R_8$, and $R_9$ are independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$ and $NH_2$.

2. The method according to claim 1, wherein the diiodo thyronine analogue has the formula:

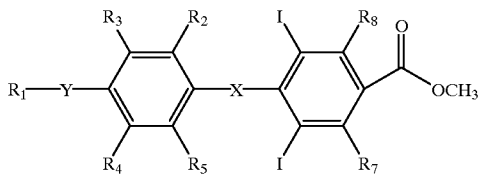

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are independently selected from the group consisting of: H, $(C_1-C_4)$ alkenyl, $(C_1-C_4)$ alkynyl, hydroxyl, $(C_1-C_4)$ alkoxy and halogen; and $R_7$ and $R_8$ are independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$ and $NH_2$.

3. The method according to claim 1, wherein the diiodo thyronine analogue is methyl 3,5-diiodo-4-(4'-methoxyphenoxy)benzoate (DIME).

4. A method of treating a viral infection in a mammal needing such treatment comprising the step of administering a pharmaceutically effective amount of a compound having no significant hormonal activity capable of binding microtubules or inhibiting microtubule formation or inhibiting tubulin polymerization wherein said compound has the structural formula:

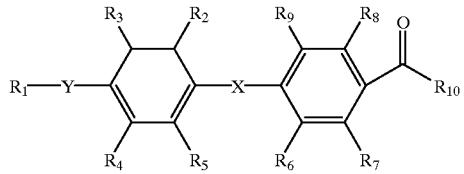

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkyl, hydroxyl, $((C_1-C_4)$ alkoxy and halogen;
$R_6$, $R_7$, $R_8$ and $R_9$ are each independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$, and $NH_2$; and
$R_{10}$ is selected from the group consisting of $(C_1-C_4)$ alkyl, $(C_1-C_4)$ alkenyl, and $(C_1-C_4)$ alkynyl.

5. The method according to claim 4 wherein the diiodo thyronine analogue has the structural formula:

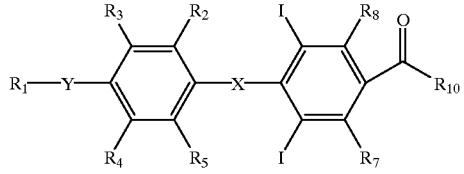

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy and halogen; $A_{,,}$ $R_7$ and $R_,$ are each independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$ and $NH_2$; and $R_{,,}$ is selected from the group consisting of $(C_1$ to $C_4)$ alkyl, $(C_1-C_4)$ alkenyl and $(C_1$ to $C_4)$ alkynyl.

6. The method of claim 1 wherein the diiodo thyronine analogue is selected from the group consisting of 1-[3,5-diiodo-4-(methoxphenoxy)pheyl]-ethanone(DIPE) and 1-[3,5-diiodo-4-(4'-methoxyphenoxy)-phenyl]-1-propanone (DIPP).

7. The method according to any one of claims 1–5 wherein the compound is administered in an amount effective to inhibit proviral DNA integration into genomic DNA of the host cell.

8. The method according to any one of claims 1–5 wherein the viral infection is caused by a virus selected from the group consisting of human immunodeficiency virus, an influenza virus, a herpes simplex virus (HSV) and a hepatitis virus.

9. The method according to claim any one of claims 3–7 wherein the viral infection is caused by HIV.

10. The method according to any one of claims 1–5 wherein the compound is administered orally.

11. A method of treating a viral infection comprising the step of administering a pharmaceutically effective amount of a composition comprising a diiodo thyronine analogue wherein the diiodo thyronine analogue has the structural formula:

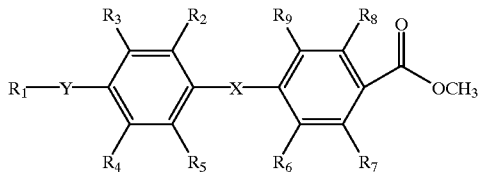

and pharmaceutically acceptable salts thereof, wherein:

$X=O$, S, $CH_2$, carboxy or absent;

$Y=O$ or S;

$R_1$=methyl or ethyl;

$R_2$, $R_3$, R, and $R_5$ are independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy and halogen; and $R_6$, $R_7$, $R_8$ and $R_9$ are independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$ and $NH_2$.

12. The method according to claim 11 wherein the viral infection is HIV.

* * * * *